United States Patent [19]

Johnson

[11] Patent Number: 5,562,668
[45] Date of Patent: Oct. 8, 1996

[54] TENSION DEVICE FOR ANCHORING LIGAMENT GRAFTS

[76] Inventor: David P. Johnson, Woodland Lodge, 69 Cleveland Road, Failand, Bristol BS8 3UL, United Kingdom

[21] Appl. No.: 430,293

[22] Filed: Apr. 28, 1995

Related U.S. Application Data

[63] Continuation-in-part of Ser. No. 966,182, filed as PCT/GB91/01295, Jul. 30, 1991 published as WO92/02196, Feb. 20, 1992, abandoned.

[51] Int. Cl.⁶ ................................................ A61B 17/68
[52] U.S. Cl. ................................. 606/72; 606/86; 623/13
[58] Field of Search ................................... 606/65, 66, 73, 606/86, 53, 72, 105, 99, 90; 623/13, 16, 20

[56] References Cited

U.S. PATENT DOCUMENTS

| | | | |
|---|---|---|---|
| 4,708,132 | 11/1987 | Silvestrini | 606/86 |
| 4,776,851 | 10/1988 | Bruchman | 623/13 |
| 4,870,957 | 10/1989 | Goble et al. | 623/13 |
| 4,955,910 | 9/1990 | Bolesky | 623/13 |
| 4,997,433 | 3/1991 | Goble et al. | 606/64 |
| 5,002,574 | 3/1991 | May et al. | 623/13 |
| 5,108,431 | 4/1992 | Masat et al. | 623/13 |
| 5,108,433 | 4/1992 | May et al. | 623/13 |
| 5,151,104 | 9/1992 | Kenna | 606/73 |
| 5,152,790 | 10/1992 | Rosenberg et al. | 623/13 |

FOREIGN PATENT DOCUMENTS

| | | | |
|---|---|---|---|
| 2614123 | 10/1977 | Germany | 623/13 |

*Primary Examiner*—Guy V. Tucker
*Attorney, Agent, or Firm*—Michael D. Bednarek; Kilpatrick & Cody

[57] ABSTRACT

A screw tensioning device is proposed for holding at least one end of a ligament graft. The device has a thimble (1) which locates in the mouth of a drilling through bone, a nut (2) captively seated in the thimble, and an anchorage element (3) with a screw threaded stud (12) which can engage the nut. Different forms of anchorage elements are provided for different grafts, but each is adapted to securely hold one end of a ligament graft. The anchorage element (3) with a ligament attached is drawn through the drilling from the opposite side to the thimble (1) until the stud (12) engages the nut (2). The nut is then turned by a tool (19) until the required tension is achieved.

8 Claims, 1 Drawing Sheet

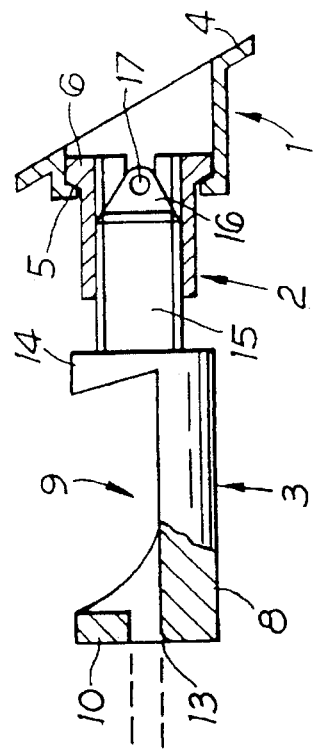
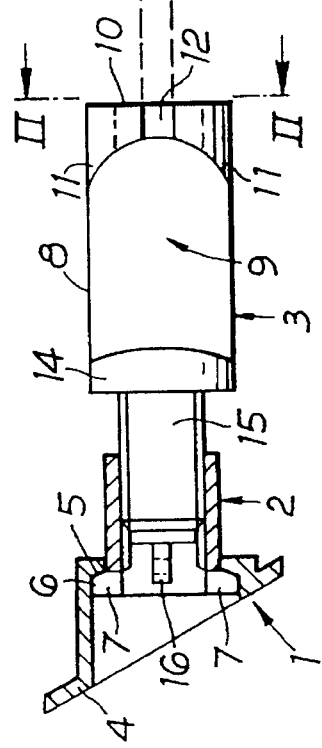
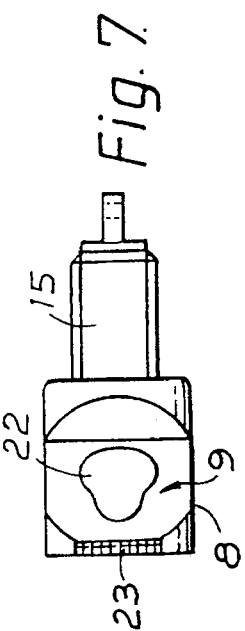
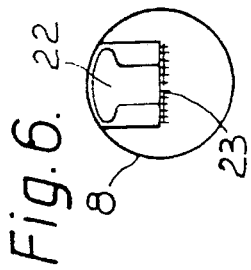
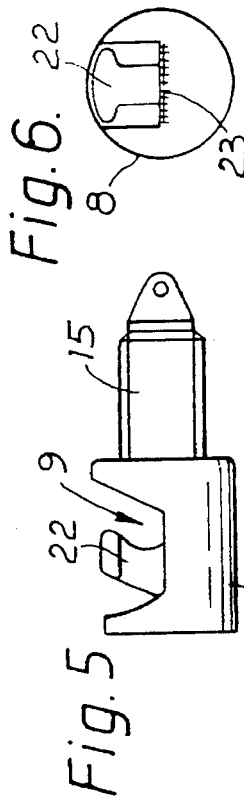
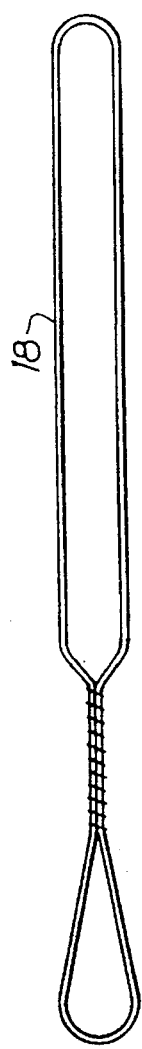
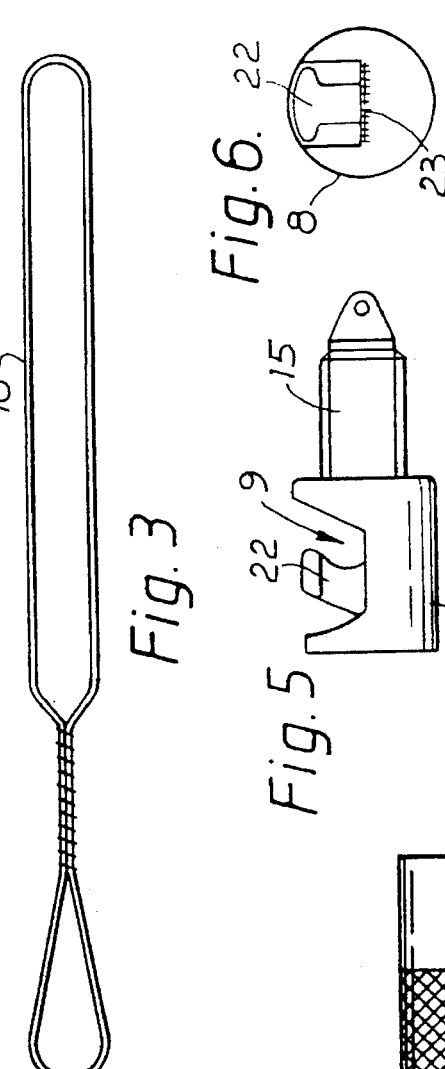
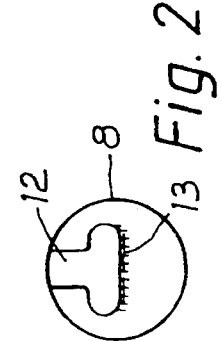

TENSION DEVICE FOR ANCHORING LIGAMENT GRAFTS

BACKGROUND OF THE INVENTION

This application is a continuation of application Ser. No. 07/966,182, filed Feb. 19, 1993, now abandoned, and which was filed as PCT/GB91/01295 on Jul. 30, 1991, published WO92/02196, Feb. 20, 1992.

1. Field of the Invention

This invention relates to surgical devices and is concerned with an adjustable tensioning assembly for ligaments.

2. Description of Related Art

The recent treatment of chronic knee instability due to rupture of the anterior cruciate ligament has been a mixture of ligament repair, augmentation or substitution by tendon transfer. The mediocre results and the inability of most athletes to return to their previous sporting activities in full capacity has prompted intense research into prosthetic cruciate replacement (Johnson R J et al. 1984). Initial research centered upon the use of the patella tendon or tensor fascia larter. Subsequent research centered upon carbon fiber or dacron ligaments as scaffolds for the slow invasion by fibrous tissue (Butler D L et al. 1985). Recently great interest has been shown in expanded polytetrofluroethelene or "Gore-tex" ligaments. This ligament was first used in a multi center research project in 1984, and the initial good results have resulted in its wider use. However, the long term results of independent assessment suggest an incidence of chronic knee effusion and late rupture of the Gore-tex graft. As a result, the most common technique at the present time is the use of an autogenous patella tendon graft with bone harvested from the patella and the tibial tuberosity. The patella tendon graft and bone plugs are fed into tunnels within the femur and tibia and secured at each end.

One of the outstanding problems and the subject of much discussion is the isometric placement of these ligaments. Theoretically, isometric placement is possible where the ligament remains at the same tension throughout the range of knee flexion. However, this is difficult to achieve in practice. Many recent projects have defined the isometric points for insertion of the drill and have demonstrated the effect of incorrect placement. However, an unsolved problem is the fixation of the ends of the ligament with sufficient strength for early motion to be allowed. Different techniques include screws, baffles, bone blocks, staples, washers, screws and, more recently, toggles (Amis A A 1988. Good et al. 1988). These all provide support which may be unreliable and which usually require protection or cautious use for up to one year to allow adequate fibers or bony ingrowth to provide secure fixation. This delays the return to activity, particularly sports, which leads to more muscle wasting and stiffness.

The final problem, which has yet received little attention, is correct tensioning of the ligament. For the ligament to be functional it not only has to be inserted isometrically, but it has to be correctly tensioned in order to allow a full range of motion. In particular, it needs to be tight enough to give stability rather than being a check rein loaded only at the extremes of motion. With some ligaments, such as the Leeds Keio ligament, maintenance of tension during insertion is technically difficult, and early reports suggest some degree of laxity is often present post-operatively. No method of insertion is believed to be currently available such that the tension may be incrementally increased while the range of motion and stability is continuously examined.

SUMMARY OF THE INVENTION

The aim of this invention is to enable a ligament to be inserted and firmly held in position in an easy and certain manner, while allowing the tension in the ligament to be adjusted to an optimum. It may even be adjustable at a later operation if necessary. It should also be usable for a prosthetic ligament graft as well as an autogenous patella tendon graft.

According to the present invention, there is provided a tensioning device for ligament grafts, the device comprising an anchorage element for receiving and holding one end of a ligament when it is under tension and leading from one end of said element, a bone engaging thimble, and screw means located by the thimble and co-operating with said element at its other end for drawing said element and said thimble together.

To fit such a device the bone is drilled through and the anchorage element, with one end of the ligament engaged with it, is inserted through the bore from one side. The thimble is placed to abut the opposite side of the bone, having a portion which locates it partially within the other end of the bore. The screw means are then engaged and as they are tightened, the ligament is tensioned and the thimble is drawn more firmly against the bone.

Usually, there will be a pair of such devices with the other end of the ligament anchored in a similar manner, although screw-adjustability at both ends may not always be required.

In the preferred form, the thimble is generally of hollow cylindrical form having an external flange at one end and an internal shoulder at the other end, the flange being for abutment of bone around the mouth of a drilling in which the remainder of the device is received, and the shoulder being for retention of the screw means. The flange will generally be at a slant with respect to the axis of the cylinder, preferably in the range of 45°–60°, and the screw means will have an external projection for engagement of said internal shoulder of the thimble. The screw means may have a detent in its end for turning by a tool entered through the thimble, and, conveniently, it takes the form of a nut engageable on a threaded portion of said anchorage element.

The anchorage element will preferably be of generally cylindrical form co-axial with the screw means to fit snugly in the bore through the bone, but having a lateral recess to accept an end of the ligament. In one form a slot leads from said recess to said one to guide the ligament into leading substantially co-axially from said element, the portion in which the slot is formed providing an abutment for a bone fragment at the end of a harvested tendon. In another form, the recess has an upstanding abutment within the envelope of said element for the retention of the end of a prosthetic anterior cruciate graft.

BRIEF DESCRIPTION OF THE DRAWINGS

For a better understanding of the invention, one embodiment will not be described, by way of example, with reference to the accompanying drawing in which:

FIG. 1 is a side view, partially in longitudinal section, of a ligament tensioning device, FIG. 2 is a section on the line II—II of FIG. 1, FIG. 3 shows a lead wire for use with the device, FIG. 4 is a side view of a tensioning key for use with the device, and FIGS. 5–7 show views of an alternative carrier that could be incorporated in the device.

DETAILED DESCRIPTION OF THE DRAWINGS

Reference will be made to inner and outer ends, these being with reference to the mid-point of the assembly.

At each end the tensioning device comprises a thimble 1 outermost, an intermediate nut 2, and a carrier 3 innermost. At the left hand end the carrier 3 is shown rotated through 90° from identical orientation with the carrier at the right hand end.

Each thimble 1 is of squat cylindrical form with its outer end angled and having an external flange 4. This angle is preferably between 45° and 60° to the axis. Internally, the thimble has a thickened portion towards its inner end to form a shoulder 5.

Each nut 2 is basically a hollow internally screw-threaded cylinder with an external rim 6 at its outer end, the underside of which co-operates with the shoulder 5 of the associated thimble. At this end, diametrically opposite zones are cut away to form slots 7. At the inner end, there is an internal bevel to facilitate coupling to the carrier 3. The nuts 2 may be provided in various lengths.

Each carrier 3 has a main body 8 having a cylindrical envelope, but this has a middle portion cut away to form a recess 9. At its inner end, the wall 10 defining the limit of the recess is shaped with re-inforcing shoulders 11 and is cut away in a T-shaped slot 12 as best seen in FIG. 2. The cross arm of the T opens to the base of the recess 9 and is virtually diametral of the inner end of the carrier. Where it emerges to the end face, there is a rounded or bevelled edge 13 to reduce chafe. At the outer end of the recess 9, the end wall 14 is undercut to contain the bone fragment. Beyond that there is a co-axial stud 15 externally screw threaded to mate with the nut 2. At its coned tip, which eases entry into the nut 2, the stud 12 has a transverse lug ! 16 with a small hole 17.

For fitting this device the bone is drilled through with a bore corresponding to the envelope diameter of the carriers 3, which is the same as that of the non-flanged parts of the thimbles 1. A lead wire 18 is connected to one of the carriers 3 using the hold 17. A suitable configuration for the wire 18 is shown in FIG. 3. The long loop is then passed through the bore, and also through a tensioning key 19 (FIG. 4) which is of hollow cylindrical form with a knurled portion 20 for a good grip, and two lugs 21 at one end to cooperate with the slots 7. The carrier 3, with a bone fragment located in the recess 9 and the attached tendon leading through the slot 12, is drawn up the bore until the stud 15 engages the nut 2, which can then be turned using the key 19 to complete the tensioning. Once that is done, the key can be removed, and then the lead wire 18.

This assumes that the ligament is already anchored at the other end. If it is not, then of course there will be no tension, and the nut is simply done up a number of turns to ensure a good grip, while allowing for later adjustment.

The alternative carrier of FIG. 5 differs by having a bollard 22 upstanding in the recess 9 and inclining towards the stud end. The undercut at that end is not required, and both end walls have generally the same configuration with the T-slot opened out into a square one 23. This bollard enables a prosthetic anterior cruciate graft to be coupled as an alternative to an autogenous patella tendon.

I claim:

1. A tensioning device for ligament grafts, the device comprising:
   a bone engaging thimble;
   a generally cylindrical anchorage element having a cylindrical wall, a central longitudinal axis, a first end wall facing the thimble, and a second end wall facing away from the thimble;
   screw means cooperating coaxially with said first end wall of the anchorage element for drawing said anchorage element and said thimble together;
   a lateral recess formed in a first portion of the cylindrical wall of the anchorage elements, the recess extending from an external surface of the cylindrical wall to the central longitudinal axis of the anchorage element, to accept and retain, in use, an end of a ligament graft;
   a second portion of said cylindrical wall dividing said lateral recess from said second end wall of the anchorage element;
   a hole extending through said second end wall substantially along said central longitudinal axis from an external end surface of said second end wall to communicate with said lateral recess; and
   a slot formed in said second portion of the cylindrical wall and in a radial outer edge of said second end wall, said slot being open at both ends and extending longitudinally from said recess to said external end surface of said second end wall and radially inwards from a radial outer edge of said second portion of the cylindrical wall and the radial outer edge of the second end wall to communicate with said hole, thereby permitting, in use, a portion of a ligament graft adjacent the lateral recess to be passed laterally inwards through the slot to lie within the hole so as to align substantially co-axially with said longitudinal axis of said anchorage element, and wherein the hole and the slot form an opening in the second end wall having a transverse cross-sectional area smaller than a transverse cross-sectional area of said recess.

2. A device as claimed in claim 1, wherein said bone engaging thimble is of hollow cylindrical form having an external flange at one end and an internal shoulder at the other end, the flange being for abutment of bone around the mouth of a drilling in which the remainder of the device is received, and the shoulder being for location and retention of the screw means, which has an external projection for engagement of said shoulder.

3. A device as claimed in claim 2, wherein the flange is at a slant with respect to an axis of the thimble.

4. A device as claimed in claim 2 or 3, wherein the screw means has a detent in one end for turning by a tool entered through the thimble.

5. A device as claimed in claim 1, wherein the screw means is a nut engageable on a threaded portion of said anchorage element.

6. A device as claimed in claim 1, wherein said second portion of the cylindrical wall in which the slot is formed provides a surface facing toward said thimble for abutting a bone fragment at the end of a harvested tendon.

7. A device as claimed in claim 1, further comprising a bollard fixed within the recess to said anchorage element within a substantially cylindrical envelope of said cylindrical wall of the anchorage element for the retention, in use, of an end of a prosthetic anterior cruciate graft.

8. A tensioning device for ligament grafts, the device comprising:
   a bone-engaging thimble;
   a generally cylindrical anchorage element having a cylindrical wall, a central longitudinal axis, a first end wall facing the thimble, and a second end wall facing away from the thimble;
   screw means cooperating with said first end wall of the anchorage element for drawing said anchorage element and said thimble together;

a recess formed in the cylindrical wall of the anchorage element, the recess extending from the external surface of the cylindrical wall to the central longitudinal axis of the anchorage element, to accept and retain, in use, an end of a ligament graft;

a hole extending through said second end wall of the anchorage element substantially along said central longitudinal axis from an external end surface of said second end wall to communicate with said recess for the passage through said hole, in use, of the ligament graft; and a slot linking the recess to the hole, said slot being open at both ends and extending longitudinally from said recess to said external end surface of said second end wall and radially inwards from a radial outer edge of said cylindrical wall and a radial outer edge of the second end wall to communicate with said hole to allow passage of the ligament graft or insertion of the ligament graft laterally inwards into said anchorage element, and wherein the hole and the slot form an opening in the second end wall having a transverse cross-sectional area smaller than a transverse cross-sectional area of said recess.

* * * * *

UNITED STATES PATENT AND TRADEMARK OFFICE
CERTIFICATE OF CORRECTION

PATENT NO.    : 5,562,668
DATED         : October 8, 1996
INVENTOR(S)   : David P. Johnson It is certified that error appears in the above-identified patent and that said Letters Patent is hereby corrected as shown below:

On the cover page, Item [63], in Related U.S. Application Data, "Continuation-in-part" should read --Continuation--.

Signed and Sealed this

Twenty-fourth Day of February, 1998

*Attest:*

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,562,668
DATED : October 8, 1996
INVENTOR(S) : David P. Johnson

It is certified that error appears in the above-identified patent and that said Letters Patent is hereby corrected as shown below:

On the first page, the foreign application priority data
should be inserted to read --G. Britain .....9016761.0...7-31-1990--.

Signed and Sealed this

Second Day of February, 1999

Attest:

Attesting Officer

*Acting Commissioner of Patents and Trademarks*